US011950911B2

(12) United States Patent
Rundo et al.

(10) Patent No.: US 11,950,911 B2
(45) Date of Patent: Apr. 9, 2024

(54) METHOD OF PROCESSING ELECTROPHYSIOLOGICAL SIGNALS TO COMPUTE A VIRTUAL VEHICLE KEY, CORRESPONDING DEVICE, VEHICLE AND COMPUTER PROGRAM PRODUCT

(71) Applicant: STMicroelectronics S.r.l., Agrate Brianza (IT)

(72) Inventors: Francesco Rundo, Gravina di Catania (IT); Sabrina Conoci, Tremestieri Etneo (IT); Concetto Spampinato, Catania (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 874 days.

(21) Appl. No.: 17/009,503

(22) Filed: Sep. 1, 2020

(65) Prior Publication Data

US 2021/0068739 A1    Mar. 11, 2021

(30) Foreign Application Priority Data

Sep. 9, 2019   (IT) .................. 102019000015926

(51) Int. Cl.
*G06F 21/32*   (2013.01)
*A61B 5/00*   (2006.01)
(Continued)

(52) U.S. Cl.
CPC ............ *A61B 5/18* (2013.01); *A61B 5/02416* (2013.01); *A61B 5/117* (2013.01); *A61B 5/7225* (2013.01);
(Continued)

(58) Field of Classification Search
CPC ......... G06F 21/32; A61B 5/18; A61B 5/2416; A61B 5/117; A61B 5/7225; A61B 5/7246; A61B 5/7264; G06N 3/045
See application file for complete search history.

(56) References Cited

U.S. PATENT DOCUMENTS 10,650,824 B1 *  5/2020  Kesharaju ............... G10L 17/00
2008/0101512 A1   5/2008  Mohamed et al.
(Continued)

FOREIGN PATENT DOCUMENTS

GB   2570535 A    7/2019
WO   2004107963 A2   12/2004

OTHER PUBLICATIONS

Jonnalagadda, V., "Sparse, Stacked and Variational Autoencoder," Dec. 6, 2018, 15 pages, retrieved from https://medium.com/@venkatakrishna.jonnalagadda/sparse-stacked-and-variatinoal-autoencoder-efe5bfe73b64 (retrieved on May 4, 2020).

(Continued)

*Primary Examiner* — Thaddeus J Plecha
(74) *Attorney, Agent, or Firm* — Slater Matsil, LLP

(57) ABSTRACT

An embodiment method comprises collecting at least one electrophysiological signal of a human over a limited time duration, and computing a set of electrophysiological signal features. The computing comprises at least one of: providing at least one reference electrophysiological signal and applying dynamic time warping processing to the at least one collected and at least one reference electrophysiological signals, applying stacked-auto-encoder artificial neural network processing to the collected electrophysiological signal, or filtering the electrophysiological signal collected via joint low-pass and high-pass filtering. The method further comprises applying pattern recognition processing to the computed set of features, producing a virtual key signal indicative of an identity of the human, and applying the virtual key (Continued)

signal to a user circuit to switch it between a first state and a second state as a result of the virtual key signal matching an authorized key signal stored in the user circuit.

20 Claims, 8 Drawing Sheets

(51) Int. Cl.
    *A61B 5/024*     (2006.01)
    *A61B 5/117*     (2016.01)
    *A61B 5/18*     (2006.01)
    *G06N 3/045*     (2023.01)

(52) U.S. Cl.
    CPC .......... *A61B 5/7246* (2013.01); *A61B 5/7264* (2013.01); *G06F 21/32* (2013.01); *G06N 3/045* (2023.01)

(56) References Cited

U.S. PATENT DOCUMENTS

| | | | |
|---|---|---|---|
| 2008/0103403 | A1 | 5/2008 | Cohen |
| 2010/0042172 | A1 | 2/2010 | Armoundas |
| 2012/0123232 | A1 | 5/2012 | Najarian et al. |
| 2015/0257668 | A1 | 9/2015 | Braojos Lopez et al. |
| 2016/0183812 | A1* | 6/2016 | Zhang .................... G07C 9/37 600/301 |
| 2018/0214088 | A1 | 8/2018 | Newberry |
| 2018/0249960 | A1 | 9/2018 | Gupta et al. |
| 2018/0330178 | A1 | 11/2018 | el Kaliouby et al. |
| 2019/0021615 | A1 | 1/2019 | Rundo et al. |
| 2019/0156934 | A1 | 5/2019 | Kataoka |
| 2019/0159735 | A1 | 5/2019 | Rundo et al. |
| 2019/0166122 | A1* | 5/2019 | Mochizuki .......... H04L 63/0861 |
| 2020/0156648 | A1 | 5/2020 | Zhang et al. |
| 2020/0285873 | A1* | 9/2020 | Condon ................. G06V 40/15 |
| 2020/0324784 | A1* | 10/2020 | Liang ................... G06V 20/597 |
| 2020/0330020 | A1 | 10/2020 | Rundo et al. |

OTHER PUBLICATIONS

Moller, M., "A Scaled Conjugate Gradient Algorithm for Fast Supervised Learning," Neural Networks, Elsevier Science Publishers, vol. 6, No. 4, Jan. 31, 1993, pp. 525-533, Barking, GB.
Wikipedia, "Sofmax function," Sep. 2, 2019, retrieved from https://en.wikipedia.org/w/index.php?title=Softmax_function&oldid=913685380 (retrieved on May 4, 2020), 8 pages.
Wikipedia, "Dynamic time warping," Aug. 20, 2019, 7 pages, retrieved from https://en.wikipedia.org/w/index.php?title=Dynamic_time_warping&oldid=911733837 (retrieved on May 4, 2020).
Agro, D., et al. "PPG Embedded System for Blood Pressure Monitoring", AEIT Annual Conference—From Research to Industry: The Need for a More Effective Technology Transfer (AEIT), Trieste, Sep. 18-19, 2014, 6 pages.
Bengio, Yoshua, "Learning Deep Architectures for AI", Foundations and Trends® in Machine Learning: vol. 2: Issue. 1, Jan. 2009, Canada, 56 pages, http://dx.doi.org/10.1561/2200000006.
Bolanos, M., et al., "Comparison of heart rate variability signal features derived from electrocardiogramand photoplethysmography in healthy individuals", Proceedings of the 28th IEEE EMBS Annual International Conference, New York City, USA, Aug. 30-Sep. 3, 2006, 6 pages.
Jeyhani, Vala et al., "Comparison of HRV parameters derived from photoplethysmography and electrocardiogra signals", 2015 37th Annual International Conference of the IEEE Engineering in Medicine and Biology Society (EMBC) Aug. 25-29, 2015, 4 pages.
Kurian, Deepu et al., "Drowsiness Detection Using Photoplethysmography Signal," IEEE Fourth International Conference on Advances in Computing and Communications, Aug. 27-29, 2014, 4 pages.
Lee, B-G., et al., "Real-time physiological and vision monitoring of vehicle driver for non-intrusive drowsiness detection", IET Communications, vol. 5, Issue 17, Nov. 25, 2011, p. 2461-2469.
Mazzillo, M., et al., "Silicon Photomultiplier Technology at STMicroelectronics", IEEE Transactions on Nuclear Science, vol. 56, No. 4, Sep. 2009, pp. 243-2442.
Mazzillo, Massimo et al., "Electro-Optical Performances of p-on-n and n-on-p Silicon Photomultipliers", IEEE Trans. Electron Devices, vol. 59, No. 12, Dec. 2012, pp. 3419-3425.
Rundo, Francesco, et al., "An Advanced Bio-Inspired PhotoPlethysmoGraphy (PPG) and ECG Pattern Recognition System for Medical Assessment", Sensors, vol. 18, No. 2, Jan. 30, 2018, 22 pages.
Ryu, Gi-Seong et al., "Flexible and Printed PPG Sensors for Estimation of Drowsiness," IEEE Transactions on Electron Devices, vol. 65, No. 7, Jul. 2018, 8 pages.
Sari, Nila Novita et al., "A two-stage intelligent model to extract features from PPG for drowsiness detection," 2016 International Conference on System Science and Engineering (ICSSE) Jul. 7-9, 2016, 2 pages.
Spachos, Petros et al., "Feasibility Study of Photoplethysmographic Signals for Biometric Identification", 17th International Conference on Digital Signal Processing (DSP), Greece, Jul. 2011, pp. 1-5.
Szankin, M., et al., "Long Distance Vital Signs Monitoring with Person Identification for Smart Home Solutions", 40th Annual International Conference of the IEEE Engineering in Medicine and Biology Society (EMBC), Jul. 2018, pp. 1558-1561.
Vicente, Jose, et al., "Detection of Drive's Drowsiness by means of HRV Analysis", IEEE Computing in Cardiology, Sep. 18-21, 2011, 4 pages.
Wan, Yongbo, et al., "Design of a Photoplethysmographic Sensor for Biometric Identification", International Conference on Control, Automation and Systems, Oct. 17-20, 2007, pp. 1897-1900.
Yao, Jianchu et al., "A Pilot Study on Using Derivatives of Photoplethysmographic Signals as a Biometric Identifier", 29th Annual International Conference of the IEEE Engineering in Medicine and Biology Society, Aug. 22-26, 2007, pp. 4576-4579.
Wikipedia, "Sofmax function", Sep. 2, 2019, 8 pages, retrieved from https://en.wikipedia.org/w/index.php?title=Softmax_function&oldid=913685380 (retrieved on May 4, 2020).

* cited by examiner

METHOD OF PROCESSING ELECTROPHYSIOLOGICAL SIGNALS TO COMPUTE A VIRTUAL VEHICLE KEY, CORRESPONDING DEVICE, VEHICLE AND COMPUTER PROGRAM PRODUCT

CROSS-REFERENCE TO RELATED APPLICATIONS

This application claims the benefit of Italian Application No. 102019000015926, filed on Sep. 9, 2019, which application is hereby incorporated herein by reference.

TECHNICAL FIELD

The description relates to processing electrophysiological signals such as, e.g., PhotoPlethysmoGraphy (PPG) signals.

One or more embodiments may be useful in obtaining in-vehicle biometric information from the living body of the driver of a vehicle with a view to possibly performing personal authentication and activating tailored vehicle functionalities.

BACKGROUND

Generally PhotoPlethysmoGraphy (PPG) is a simple and low-cost optical technique that can be used to detect blood volume changes in the microvascular bed of human tissue. PhotoPlethysmoGraphy is often used in a non-invasive manner to make measurements at the skin surface.

A PPG waveform comprises a pulsatile ('AC') physiological waveform which can be attributed to cardiac-synchronous changes in the blood volume with each heartbeat, superimposed on a slowly varying ('DC') baseline with various lower frequency components which can be attributed to respiration, thermoregulation, the nature of skin tissues, and so on.

For each cardiac cycle, the heart pumps blood to the periphery. This pressure pulse is somewhat damped by the time it reaches the skin, but is enough to distend the arteries and arterioles in the subcutaneous tissue. If a light reflex/transmit detector device is attached over the skin, a pressure pulse can also be seen from the venous plexus, as a small secondary peak.

The change in volume caused by the pressure pulse can be detected by illuminating the skin with light from a light-emitting diode (LED) and then by measuring the amount of light either transmitted or reflected to a photodiode. Each cardiac cycle appears as a peak.

Blood flow to the skin can be modulated by multiple other physiological systems and PPG can also be used to monitor breathing, hypovolemia, and circulatory conditions as well as for subjective analysis.

Additionally, the shape of the PPG waveform differs from subject to subject, and varies with the location and manner in which the pulse oximeter is attached.

Photoplethysmography (PPG) signals contain rich personal information that can be used to distinguish individual subjects.

Photoplethysmography (PPG) signals are easy to obtain with low cost, which enhances its potential to server as biometric identification mechanism for various applications.

The authentication by use of biometric information is a system by which a personal authentication is done on the basis of human physical traits of a user, namely, biological information such as fingerprint, iris, or the like.

PPG signals can be easily obtained with low cost equipment and they may found use in biometric identification mechanism.

Several approaches are proposed in literature, for instance in:

M. Szankin et al., "Long Distance Vital Signs Monitoring with Person Identification for Smart Home Solutions", 2018 40*th Annual International Conference of the IEEE Engineering in Medicine and Biology Society (EMBC)*, Honolulu, HI, 2018, pp. 1558-1561, doi: 10.1109/EMBC.2018.8512509 discusses imaging photoplethysmography, already been proved to be successful in short distance (below 1 m), in the context of the possible scenarios that system designers must have in mind include monitoring of the vital signs of residents in nursing homes, disabled people, who can't move, constant support for people regardless of the performed activity (e.g. during sleeping), infants, etc., verifying the possibility of remote pulse estimation at a distance above 5 m, integrating deep learning algorithm for person tracking and identification, even when facial features are not visible, enabling the collection of user specific measurements to create personalized vital signs patterns and providing the support for monitoring of multiple people using one video stream;

B. -. Lee, S. -. Jung and W. -. Chung, "Real-time physiological and vision monitoring of vehicle driver for non-intrusive drowsiness detection," in *IET Communications*, vol. 5, no. 17, pp. 2461-2469, 25 Nov. 2011, doi: 10.1049/iet-com.2010.0925 discusses an approach to detect driver's drowsiness by applying two distinct methods in computer vision and image processing to combine both methods under one single profile instead of relied solely on a detection method to enhance the driver's drowsiness detection resolution; therefore a non-intrusive drowsy-monitoring system is developed to alert the driver if driver falls into low arousal state, wherein photoplethysmography (PPG) is analyzed for its changes in signals waveform from awake to drowsy state meanwhile eyes pattern or motion in image processing is addressed to detect driver fatigue;

Yongbo Wan, Xiaodong Sun and Jianchu Yao, "Design of a Photoplethysmographic Sensor for Biometric Identification," 2007 *International Conference on Control, Automation and Systems*, Seoul, 2007, pp. 1897-1900, doi: 10.1109/ICCAS.2007.4406656 discusses the design of an analog amplification circuit for PPG signals to remove the DC component of the signal, by adding an amplifier bias-adjusting circuit, a high signal-to-noise ratio AC signal can be acquired from the raw PPG signal, wherein hardware improvement results in better signal quality and makes identification data-processing easier;

J. Yao, X. Sun and Y. Wan, "A Pilot Study on Using Derivatives of Photoplethysmographic Signals as a Biometric Identifier," 2007 *29th Annual International Conference of the IEEE Engineering in Medicine and Biology Society*, Lyon, 2007, pp. 4576-4579, doi: 10.1109/IEMBS.2007.4353358 discusses two important issues in applying derivatives of PPG signals as discriminants to identify and verify subjects: consistency within an individual subject and discriminability between different subjects. The experimental results demonstrate that, by employing statistical tools, derivatives can precisely describe the features of an individual's PPG signal and be used as bio-measures for identification purposes;

P. Spachos, Jiexin Gao and D. Hatzinakos, "Feasibility study of photoplethysmographic signals for biometric identification," 2011 17th International Conference on Digital Signal Processing (DSP), Corfu, 2011, pp. 1-5, doi: 10.1109/ICDSP.2011.6004938 discusses the feasibility, along with the relevant signal processing methods, of using PPG signals of an individual as a biometric trait, wherein PPG signals from two biometric datasets are examined, wherein PPG signals were obtained from the fingertips of 29 healthy subjects, wherein experimental results demonstrate that PPG signals can be used as bio-measures for identification purposes given that PPG signals are collected under controlled environment and with accurate sensors.

Various solutions proposed in the literature may be exposed to one or more of the following drawbacks:

lack of robustness and low accuracy;
frequency-analysis based methods result in slow and time-consuming processing;
noise and signal stabilization issues.

In general, existing solutions do not provide a suitable reliability, e.g., especially while employing relatively cheap and low complexity components.

SUMMARY

An object of one or more embodiments is to contribute in providing such an improved solution.

According to one or more embodiments, that object can be achieved by means of a method having the features set forth in the claims that follow.

A method of processing electrophysiological signals for identifying the car-driver by means of physiologic bio-signals, e.g. physio-fingerprint, may be exemplary of such a method.

One or more embodiments may relate to a corresponding vehicle-key device.

A vehicle-key button device including a PPG sensor and configured to perform one or more embodiments of the electrophysiological signals processing method may be exemplary of such a system.

One or more embodiments may relate to a vehicle equipped with one or more embodiments of the vehicle-key device.

In one or more embodiments the method may be a computer-implemented method.

One or more embodiments may include a computer program product loadable in the memory of at least one processing circuit (e.g., a computer) and including software code portions for executing the steps of the method when the product is run on at least one processing circuit. As used herein, reference to such a computer program product is understood as being equivalent to reference to a computer-readable medium containing instruction for controlling the processing system in order to co-ordinate implementation of the method according to one or more embodiments. Reference to "at least one computer" is intended to highlight the possibility for one or more embodiments to be implemented in modular and/or distributed form.

The claims are an integral part of the technical teaching provided herein with reference to the embodiments.

One or more embodiments may involve a pipeline configured for processing PhotoPlethysmoGraphy (PPG) signals based on the use detectors such as e.g. of Silicon PhotoMultiplier (SiPM) detectors. Such probe sensors may provide advantages in terms of single-photon sensitivity and high internal gain for relatively low reverse bias.

One or more embodiments may adopt (possibly in connection with SiPM detectors) a processing pipeline adapted to correct signal distortion.

One or more embodiments may adopt a processing pipeline including a PPG raw signal filter, in turn including an e.g. FIR pass-band scheme (e.g. low-pass plus high-pass), a PPG pattern recognition system as well as a system for detecting and extract medical indicators.

One or more embodiments may include machine/deep learning systems facilitating robust car-driver profiling and identification.

One or more embodiments may facilitate increasing care safety and security, enhancing so-called ADAS (Advanced Driver Assistance Systems) or DADSS (Driver Alcohol Detection System for Safety) applications.

One or more embodiments may use advanced time-based algorithms for efficient and robust near-real time detection of car-driver user, by using sampled PPG signal of the same driver.

One or more embodiments may, advantageously:

avoid using frequency domain conversion or operations which may use CPU-intensive computations,
reduce an amount of instrumentation, e.g. avoiding the use of vision cameras, relying solely on a simple electrophysiological, e.g. PPG, sensor,
low CPU consuming as the method is feed-forward;
high speed re-learning (optionally) and user profile (car driver) detection (~⅘ secs),
high precision and robustness (~99.7% of accuracy),
resilience to hacking attempts.

BRIEF DESCRIPTION OF THE DRAWINGS

One or more embodiments will now be described, by way of non-limiting example only, with reference to the annexed Figures, wherein.

DETAILED DESCRIPTION OF ILLUSTRATIVE EMBODIMENTS

The In the ensuing description, one or more specific details are illustrated, aimed at providing an in-depth understanding of examples of embodiments of this description. The embodiments may be obtained without one or more of the specific details, or with other methods, components, materials, etc. In other cases, known structures, materials, or operations are not illustrated or described in detail so that certain aspects of embodiments will not be obscured.

Reference to "an embodiment" or "one embodiment" in the framework of the present description is intended to indicate that a particular configuration, structure, or characteristic described in relation to the embodiment is comprised in at least one embodiment. Hence, phrases such as "in an embodiment" or "in one embodiment" that may be present in one or more points of the present description do not necessarily refer to one and the same embodiment.

Moreover, particular conformations, structures, or characteristics may be combined in any adequate way in one or more embodiments.

The references used herein are provided merely for convenience and hence do not define the extent of protection or the scope of the embodiments.

As mentioned, the present disclosure relates to a method of processing electrophysiological signals.

For the sake of simplicity, one or more embodiments are discussed herein mainly with respect to PhotoPlethysmoGraphy (PPG) signals as electrophysiological signals. Such a type of electrophysiological signals is exemplary, being otherwise understood that one or more embodiments may be applied to virtually any electrophysiological signal which may be conveniently collected via a sensor.

Figure 1:
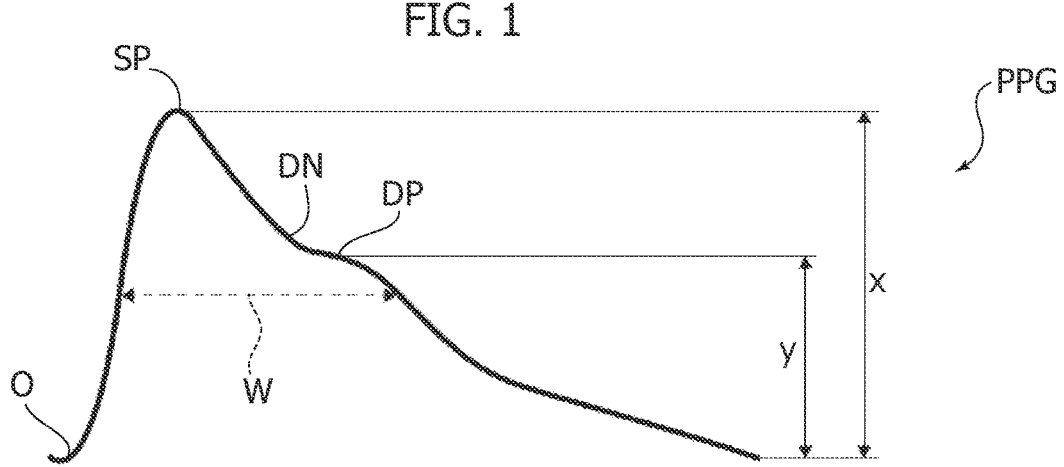
FIG. 1 is an exemplary time-diagram of a PPG waveform signal.

FIG. 1 is a diagram exemplary of a PhotoPlethysmoGraphy (PPG) signal.

As exemplified in FIG. 1, a typical PhotoPlethysmoGraphy (briefly PPG) signal/waveform comprises:
a systolic peak SP at a peak value x,
a dicrotic notch DN,
a diastolic peak DP at a value y.

A width W of the pulse may also be defined at a given value of the PPG value.

PPG signals can be detected by using PPG sensors/devices (e.g., sensor PD in FIG. 2 or sensor) comprising LED emitters operating at specific wavelengths (usually infrared at 940 nm) and silicon photomultipliers or SiPMs (see e.g. M. Mazzillo, et al.: "Silicon Photomultiplier technology at STMicroelectronics", IEEE Trans. Nucl. Sci, vol. 56, no. 4, pp. 2434-2442, 2009).

These SiPMs may have a total area of 4.0×4.5 mm2 and 4871 square microcells with 60-micron (1 micron=10-6 m) pitch. These devices have a geometrical fill factor of 67.4% and are packaged in a surface mount housing (SMD) with 5.1×5.1 mm2 total area (see e.g. M. Mazzillo, et al., cited above or M. Mazzillo, et al.: "Electro-optical performances of p-on-n and n-on-p silicon photomultipliers", IEEE Trans. Electron Devices, vol. 59, no. 12, pp. 3419-3425, 2012).

A Pixelteq dichroic bandpass filter with a pass band centered at 542 nm with a Full Width at Half Maximum (FWHM) of 70 nm (1 nm=10-9 m) and an optical transmission higher than 90% in the pass band range can be glued on the SMD package by using a Loctite® 352™ adhesive. With the dichroic filter at 3V-0V the SiPM has a maximum detection efficiency of about 29.4% at 565 nm and a PDE of about 27.4% at 540 nm (central wavelength in the filter pass band-1 nm=10-9 m). It was noted that the dichroic filter can reduce in excess of 60% the absorption of environmental light in the linear operation range of the detector operating in Geiger mode above its breakdown voltage (~27V). OSRAM LT M673 LEDs in SMD package emitting at 529 nm (1 nm=10-9 m) and based on InGaN technology have been used as optical light sources in exemplary embodiments. These LEDs have an area of 2.3×1.5 mm2, viewing angle of 120°, spectral bandwidth of 33 nm (1 nm=10-9 m) and typical power emission of a few milliWatts in the standard operation range.

Use of PPG probes comprising Silicon PhotoMultiplier (SiPM) detectors may provide advantages in terms of single-photon sensitivity and high internal gain for relatively low reverse bias.

It was observed (see e.g. D. Agrò, et al.: "PPG embedded system for blood pressure monitoring," in AEIT Annual Conference—From Research to Industry: The Need for a More Effective Technology Transfer (AEIT), Trieste, 2014), that Silicon PhotoMultipliers (SiPMs) can provide advantages in PPG systems in terms of higher AC-to-DC ratio in PPG pulse waveform, high repeatability and immunity to motion artifacts and ambient interferences. One or more embodiments as discussed herein may sense PPG signals by using SiPMs (as available with companies of the ST group) as optical probe sensors, adapted to be used in conjunction with hardware and software components in providing a signal processing pipeline.

Figure 2:
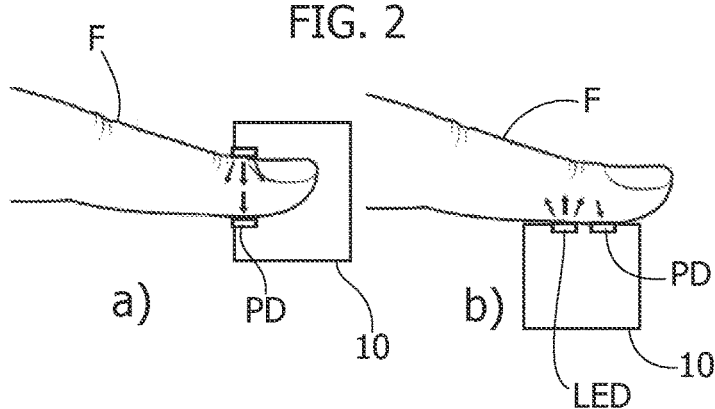
FIG. 2 is a diagram exemplary of principle underlying collecting human electrophysiological signals.

FIG. 2 is exemplary of possible operation of PPG sensors.

Light emitted by the LEDs may be absorbed by the skin (DC component) and the arteries, specifically, by oxygenated (and partly by de-oxygenated) hemoglobin (AC component).

Residual propagated/reflected (back-scattered) light may be a function (proportional-differential) of the amount of light absorbed by blood hemoglobin in the various heart phases (systolic, diastolic, dicrotic, etc.). A SiPM photomultiplier may thus detect the presence of photons in the propagated/reflected light by transducing an electrical signal that can be sampled by an e.g. 24-bit ADC thus providing PPG signal as discussed previously.

Such PPG sensors PD may be applied on a vehicle-key button SB in a vehicle V, in various arrangements as shown in FIG. 2.

One or more embodiments may take advantage of the capability of the PPG sensors PD to operate both in a transmission mode (see e.g. portion a) in FIG. 2) that is with radiation from the LED propagating through the body (e.g. the body of a patient being clinically investigated or a driver), for instance through a fingertip F, and in a reflection mode (see e.g. portion b) in FIG. 2) that is with radiation from the LED reflected (back-scattered) from the body, facilitating relaxation of the requirements for possible positioning of the PPG sensors/detectors PD with respect to the body.

Figure 3:
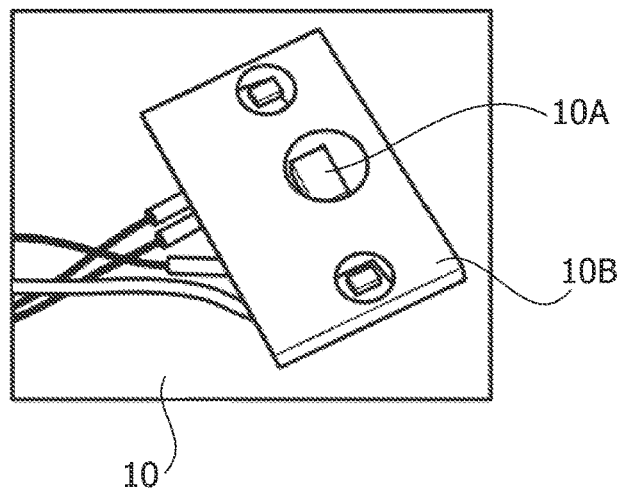
FIG. 3 is a diagram of a PPG sensor.

Specifically, as shown in FIG. 3, a PPG sensor device 10 can include a (SiPM) probe section 10A and a printed circuit board (PCB) 10B configured for interfacing the probe sections 10A with acquisition and processing circuitry.

In one or more embodiments, the printed circuit board (PCB) 10B can be designed and used to interface the PPG probe(s) and an NI (National Instrument) acquisition instrumentation during the measurement of the PPG signals. Such an acquisition and processing circuit 18 as exemplified herein may also comprise a hardware/software platform based e.g. on a personal computer (e.g. with Intel core i5 3.4 GHz plus MATLAB) configured to acquire and process electrophysiological signals.

In one or more embodiments, the probe section 10A can include SiPMs having associated, in a manner known per se, various ancillary components such as bandpass filters, LEDs, sensing resistors, bias capacitances.

One or more embodiments may comprise a vehicle V equipped with a vehicle-key device SB, 10 comprising an electrophysiological signal sensor PD configured to collect a PPG signal waveform over a limited time from a human and configured to run the processing pipeline 100.

Specifically, the sensor SB, 10 may be configured so as to collect a PPG waveform during a time interval equal to the start-up time of the engine of the vehicle V. For instance, a vehicle ignition process may be activated as a result of keeping the vehicle-key device SB, e.g. a button, for a given amount of time.

For instance, such a time duration may last approximately 50-60 seconds. For instance, the sample rate of the PPG sensor SB, 10 may be approximately around 1 kiloHertz, obtaining a time series or sampled signal S.

Figure 4:
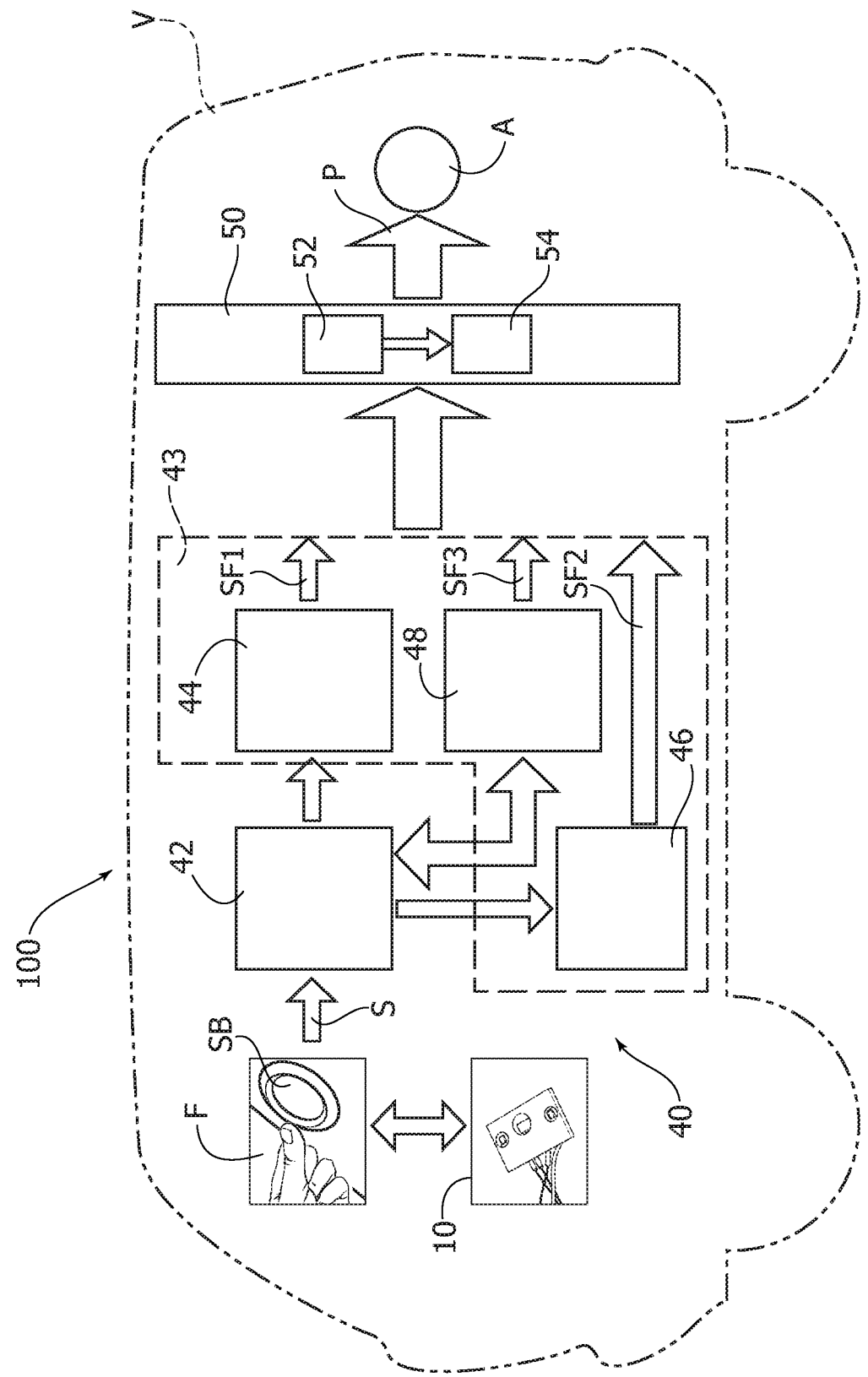
FIG. 4 is a diagram exemplary of operations of a method as per the present disclosure.

One or more embodiments as exemplified in FIG. 4, may comprise a processing pipeline 100 comprising, for instance:
- a signal pre-processing stage 42, configured to receive a (sampled) electrophysiological signal S, for instance collected by a vehicle-key device 10 as discussed in the foregoing, and to apply noise-filtering thereto; in one or more embodiments, such signal pre-processing stage 42 may use a method of processing electrophysiological signals as discussed in document US 2019/0021615 A1;
- a signal processing stage 43 configured to receive the filtered electrophysiological signal S and to extract at least one set of features SF1; SF2, SF3 therefrom, the processing stage comprising at least one of a hyper-filtering stage 44, a dynamic time warping (briefly, DTW) processing stage 46 and/or an artificial neural network (briefly, ANN) processing stage 44;
- a pattern recognition stage 50, configured to receive the at least one set of features extracted from the processed electrophysiological signal S and to apply pattern recognition processing thereto it, the pattern recognition stage 50 comprising a first pattern recognition stage 52 and a second pattern recognition stage 54 and be configured to provide a virtual key signal configured to selectively activate subsystems in the vehicle (e.g., ignition) as a function of a recognized "profile" of human vehicle drivers "matching" the electrophysiological signal features.

As mentioned, in one or more embodiments the processing pipeline 100 may be configured to provide such a virtual key signal P to a user circuit A, for instance to an electronic controller managing all subsystems in the car, or to an interface such as a display, e.g. on the dashboard of the vehicle V, to send alert signals or other signals as a function of the virtual key signal P.

In one or more embodiments, the classification stage may provide a classification signal P indicative of a profile of a human driver of a vehicle V to a user circuit A, for instance wherein the user circuit comprises a vehicle ignition/start-up circuit or a circuit configured to activate subsets of functionalities of the vehicle V.

Figure 5:
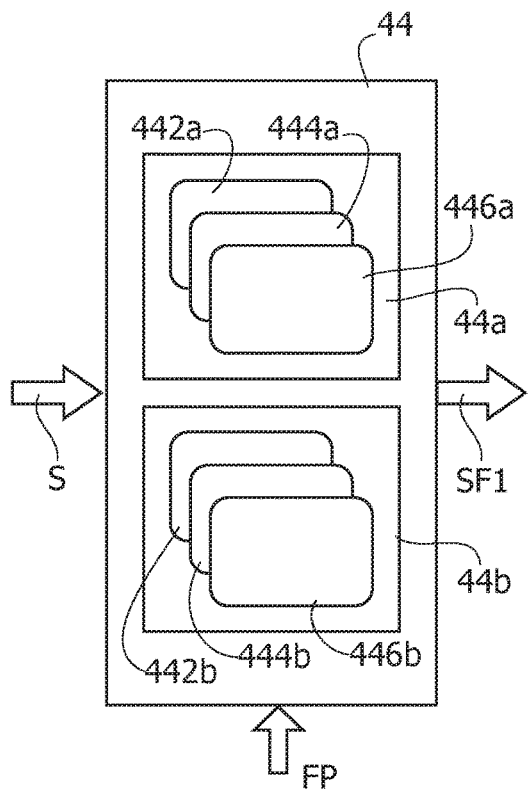
FIG. 5 is a diagram exemplary of a portion of the diagram of FIG. 4.

In one or more embodiments as exemplified in FIG. 5, the hyper-filtering stage 44 in the pipeline 40 may be configured to receive the electrophysiological signal S and apply filtering thereto, preferably passband filtering via joint concurrent high pass 44*a* and low pass filtering 44*bb*, providing a set of filtered electrophysiological signals SF1, e.g. filtered PPG signals.

It is noted that for most applications, a majority of interesting features of the electrophysiological PPG signal collected is included in a "AC" component of the PPG signal, the AC component lying e.g. in the 0.5-7.0 Hz frequency range. One or more embodiments as exemplified may thus include a filtering system (e.g. 44 in FIG. 4) active in that range.

Further frequency sub-bands of such range may be of interest to analyze, in order to extract more accurate indicators of attention level from the electrophysiological signal S. A hyper-filtering stage 44 may envisage applying multiple filtering in various frequency ranges in order to extract relevant information therefrom.

In one or more embodiments, such hyper-filtering stage 44 may be implemented in a processing circuit of a SPC58 Chorus microcontroller unit (MCU) fabricated at STMicroelectronics.

As exemplified in FIG. 5, (hyper) filtering 44 may comprise bandpass filtering via joint low-pass 44*a* and high-pass filtering 44*b*.

Inventors have observed that employing such a hyper-spectral approach may facilitate obtaining different representation of the information contained into original electrophysiological signal.

In one or more embodiments, a low-pass filtering stage 44*a* and a high-pass filtering stage 44*b* may comprise multiple filtering stages 442*a*, 444*a*, 446*a*, 442*b*, 444*b*, 446*b*, for instance:
- a first low-pass filtering stage 44*a* which may comprise a first set of filters 442*a*, 444*a*, 446*a* having a first set of filter parameters, e.g. cut-off frequencies, filter types, etc., for instance within the PPG AC component frequency range 0.5-7.0 Hz, and
- the high-pass filtering stage 44*b* may comprise a second set of filters 442*b*, 444*b*, 446*b* having a second set of parameters, e.g. cut-off frequencies, filter types, etc. for instance within the PPG AC component frequency range 0.5-7.0 Hz.

In one or more embodiments, a same number of filter stages $N_f$ may be present in the low-pass filtering stage 22*a* and high-pass filtering stage 22*b*.

In one or more embodiments, applying multiple bandpass filtering 44 to the electrophysiological signal S may facilitate obtaining different representation of information contained into original signal. Filtering with different filter types and filter parameters may facilitate obtaining multiple features of a signal at a same time, reducing the speed of processing the signal to recognize a driver profile.

For instance, the set of filtered signals SF1 may be stored in a properly defined matrix having a number of columns equal to a number n of filters employed in the third processing stage 44 and a number m of rows equal to the number of PPG signals processed.

In one or more embodiments, filtering parameters FP of the low-pass 442*a*, 444*a*, 446*a* and high-pass filters 442*b*, 444*b*, 446*b* in the third processing stage 44 may be provided.

In one or more embodiments, a set of filtering parameters FP comprising low-pass 442*a*, 444*a*, 446*a* and high-pass 442*b*, 444*b*, 446*b* filters parameters FP selected from Butterworth, Chebyshev type I, Chebyshev type II and elliptic filter parameters.

Such filter parameters may be calibrated in a calibrating stage, wherein signal output features extracted SF1 may vary as a function of the variation of the filters parameters and selecting calibrated low-pass filter parameters 442*a*, 444*a*, 446*a* and high-pass filter parameters 442*b*, 444*b*, 446*b* that provide a fit of features extracted with respect to a reference set of features extracted (e.g., known to belong to a given profile).

One or more filter parameters (e.g., cut-off frequency, number of poles, etc.) of filters of a given type, e.g. Butterworth filters, chosen for use in the set of filter stages 44*a*, 44*b*, respectively, may be calibrated via an ad-hoc Genetic Algorithm Optimization Procedure (briefly, GAOP). In one or more embodiments, such a GAOP 40 may be employed in finding optimal parameters, e.g. cut-off frequencies $\omega_c$, for each filter in the (hyper) filtering stage, for instance for the filter 442a in the first set of filters 444a. A Self-Organizing map may also be found suitable for use in combination with GAOP.

In one or more embodiments, such a third processing stage 44 may be calibrated according to a method as discussed in the Italian patent application no. 102019000005868 of the same Applicant.

Figure 6:
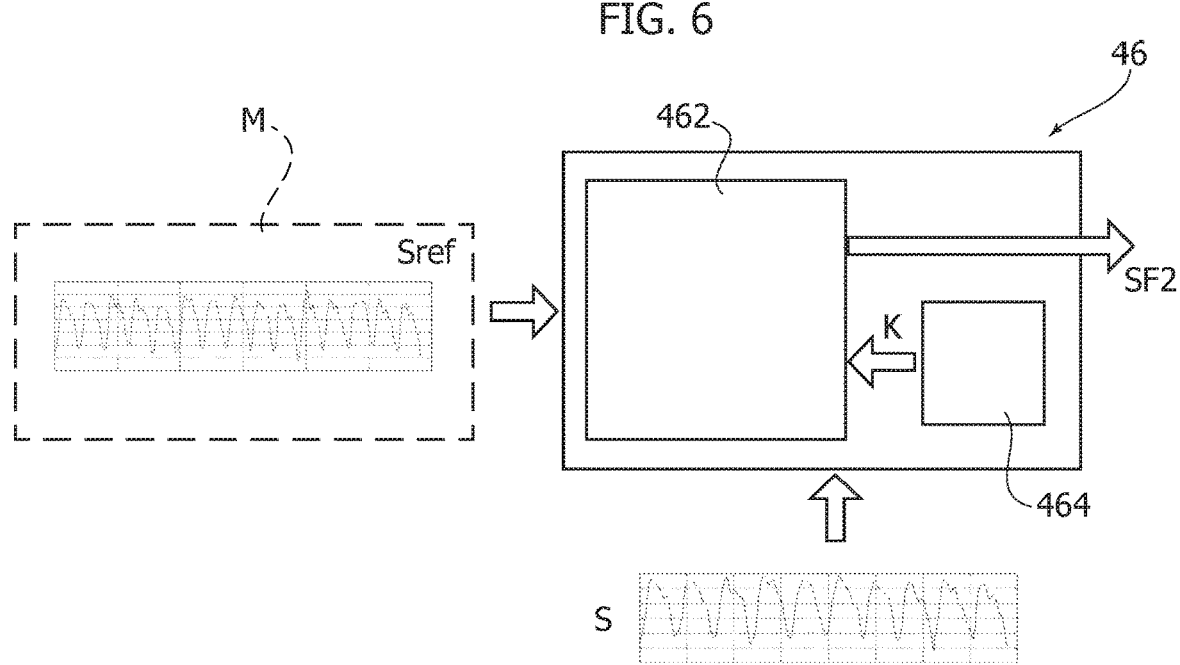
FIG. 6 is a diagram exemplary of a portion of the diagram of FIG. 4, FIGS. 7 to 9 are diagrams exemplary of possible operations of computing a virtual key signal, and FIGS. 10 to 12 exemplary of possible layouts of neural networks in embodiments.

In one or more embodiments as exemplified in FIG. 6, the DTW processing stage 46 in the pipeline 40 may comprise:
- providing a reference electrophysiological signal Sref, for instance storing a PPG signal of a vehicle driver in a memory area M in the pipeline 40 and retrieving it therefrom, and
- receiving the collected PPG signal S, and
- applying DTW processing 462 to the collected Sand to the reference electrophysiological signals Sref, the DTW processing configured to compute a set of values or features SF2 of the collected PPG signal S as a result of (temporally) aligning the collected signal onto the reference signal (or vice versa); feature values SF2 computed to perform such alignment may be indicative of a degree of similarity between the collected S and the reference Sref signals (and hence indicative of an "identity" profile of the vehicle driver).

In one or more embodiments, applying DTW processing may comprise providing a chaotic random generator 464 in order to obtain an indicator of the degree of similarity in a noisy environment, hence increasing a "weight" of the computed features.

In one or more embodiments, an ad-hoc implementation of a Needleman-Wunsch algorithm may be suitable for use in the DTW processing stage.

Figure 7:
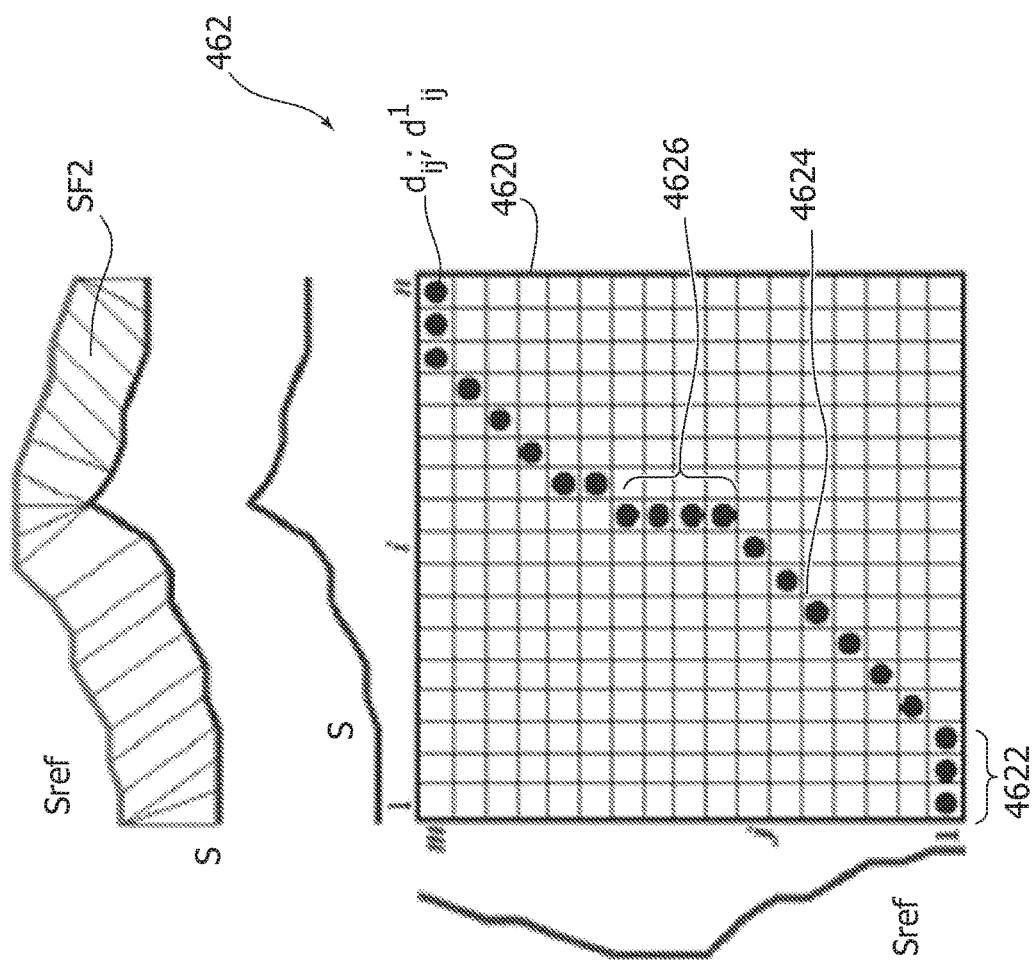

In one or more embodiments as exemplified in FIG. 7, applying DTW processing 462 may comprise:
- providing an empty grid 4620 comprising a plurality of cells, the grid configured to host a first sampled signal S on a first row and a second sampled signal Sref on a first column, wherein the empty grid has a number of rows j=1, . . . , m and a number of columns i=1, . . . , n and wherein the maximum number of rows m is a function of a number of signal samples of the reference PPG signal Sref while the maximum number of columns n is a function of a number of signal samples of the collected PPG signal S;
- providing a chaotic random generator 464 and generating at least one random value K therefrom, and
- choosing a scoring system, for instance setting a ranking equal to values of a distance (vector) d across the signal samples values of respective signals; for instance, indicating with X the first sampled signal S and with Y the second sampled signal Sref, a first distance metrics may be expressed as:

$$d_{mn}(X, Y) = \sum_{k=1}^{K}(x_{k,m} - y_{k,n})(\log x_{k,m} - \log y_{k,n})$$

and a second distance metrics may be expressed as:

$$d^1_{mn}(X, Y) = \sqrt{\sum_{k=1}^{K}(x_{km} - y_{kn})*(x_{km} - y_{k,n})}$$

where K is one random value generated from the chaotic random generator 464; using one or more metrics may facilitate obtaining multiple features;
- computing, moving through the cells of the grid row by row, a respective score $d_{ij}/d_{ij}^1$ for each (i,j) grid cell,
- selecting a "best" candidate score value (e.g., lowest/highest) for each row and/or each column.

As exemplified in FIG. 6A, as a result of the DTW processing 462, a feature or "warping path" SF2 of a signal onto another may be obtained.

DTW processing 462 may stretch two sampled signals (or vectors), x and y, onto a common set of instants such that distance, e.g. the sum of the Euclidean distances between corresponding points, is smallest. To stretch the inputs, DTW may repeat each element of x and y as many times as necessary. As a result, DTW processing may return a common set of instants, or warping path, such that x(i) and y(j) have the smallest possible distance between them.

For instance, the warping path SF2 may comprise, as exemplified in FIG. 6A, a portion indicative of an expansion 4622, a contraction 4626 or a match 4624 between collected PPG signal samples and their "parallel" group of signal samples of the reference PPG signal.

Figure 8:
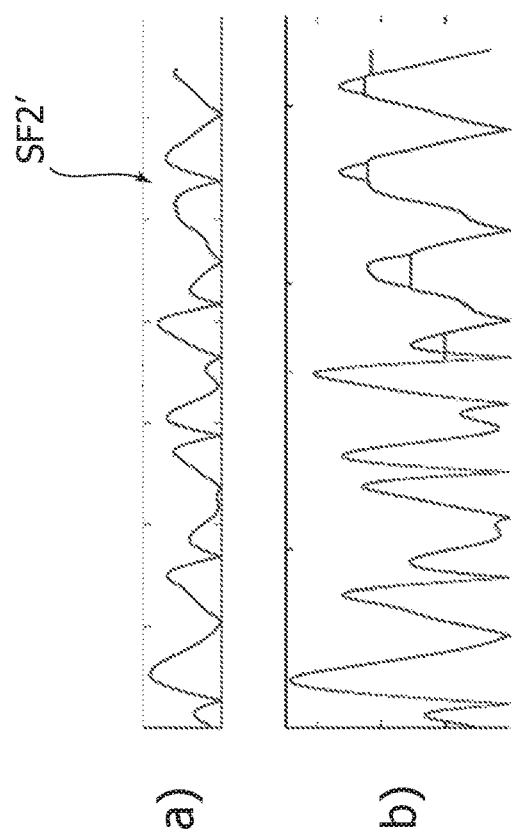
Figure 9:
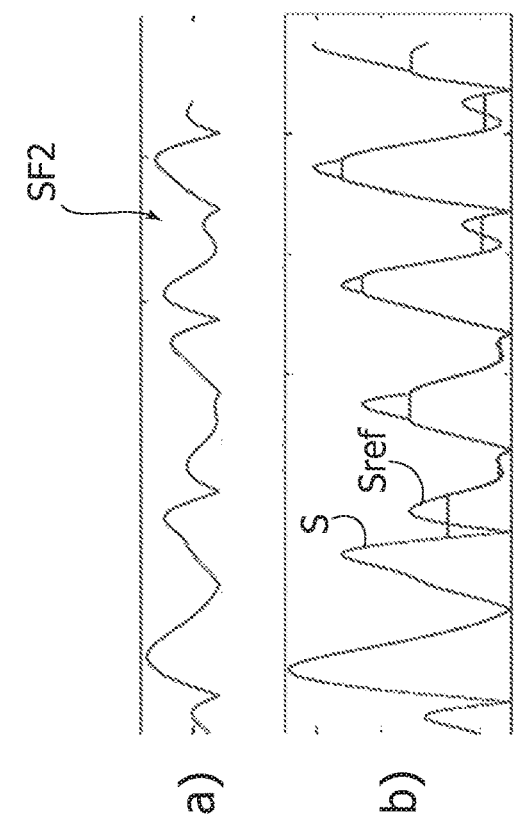

As exemplified in FIGS. 8 and 9, multiple features SF2, SF2' may be obtained from subsequent application of DTW processing 462 to the set of signals to be mapped one to another. Specifically, multiple features SF2, SF2' may differ in that a different value K generated by the random generator 464 is used to compute either one of the score metrics $d_{ij}/d_{ij}^1$, increasing the number of features which may be obtained and the robustness of the method.

In one or more embodiments, the ANN processing stage 48 in the processing stage 43 in the pipeline 40 may comprise an ANN processing stage 48.

Figure 10:
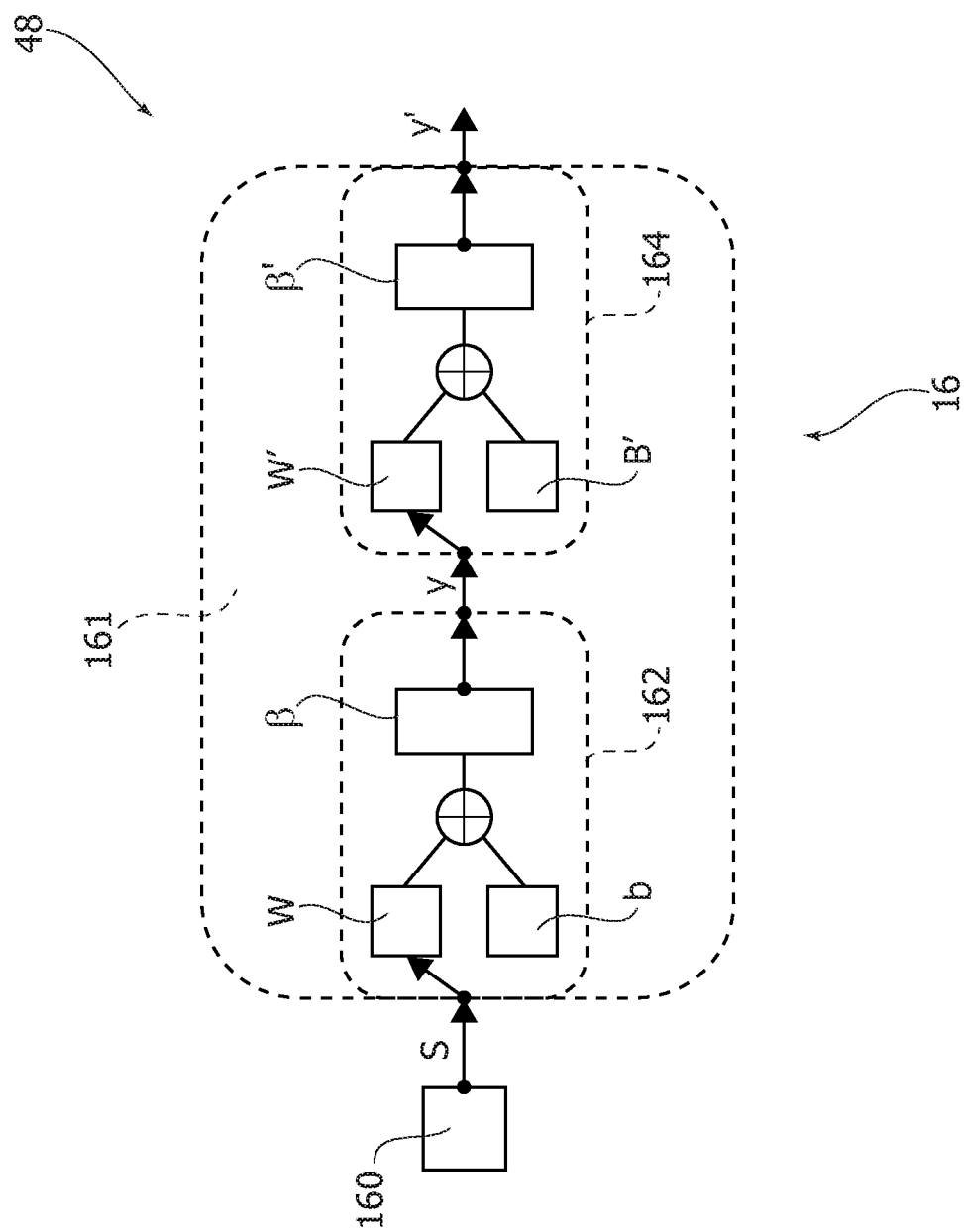

FIG. 10 is an exemplary diagram of a possible network topology of an artificial neural network (or machine learning) processing stage 48 configured to extract a set of features SF3 from the received PPG signal S.

In one or more embodiments, processing methods such as those disclosed in Yoshua Bengio (2009), "Learning Deep Architectures for AI", Foundations and Trends® in Machine Learning: Vol. 2: No. 1, pp 68-95. http://dx.doi.org/10.1561/220000006 may be found suitable for artificial neural network processing 48.

In one or more embodiments, applying neural network processing 48 may comprise an artificial neural network (briefly, ANN) processing pipeline, e.g. in a feed-forward pipeline, comprising:
- an input layer 160, configured to receive the PPG signal S, specifically to receive a set of PPG signal (samples) collected over the limited time duration of the permanence of the vehicle driver finger F onto the vehicle key button PPG sensor SB, 10;
- a first processing layer 162, coupled to the input layer 160, configured to receive the set of PPG signal samples S and provide a first set of latent representations y and a first subset of, e.g. self-learned, features W in the set of PPG signal time samples S;
- a second processing layer 164, coupled to the first processing layer 162, configured to receive such set of latent representations y and provide a second set of latent representations y' and a second subset of, e.g. self-learned, features W', e.g. self-learned in the set of PPG samples S;
- an output layer 180, coupled to the second layer 164, configured to provide the computed set of features SF3.

The input layer 160 and the output layer 180 may be indicative of a number of "slots" or "perceptrons" available for input or output in the ANN stage 48. For instance, the input layer 160 may provide space for a number of input data, e.g. for a number k of input data points equal to the number of PPG signal time samples, e.g. k=22.

In one or more embodiments, the first 162 or second 164 layers may comprise so-called "hidden layers" in which perceptrons coupled to other neurons in the network and hence not directly accessible from input and output layers, which indicate that processing may occur with a higher number and more complex architecture of perceptrons than in a single layer, for instance in order to process in parallel multiple collected PPG signals, e.g. by using 50 hidden layers.

In one or more embodiments, the first processing layer 162 and the second processing layer 164 may have a likewise Multi-Layer Perceptron (briefly, MLP) architecture, having a set of n hidden layers, for instance n=50 hidden layers.

A single i-th perceptron $\varphi_i$, e.g. in the first processing layer 162, may be identified in the set of n perceptrons by a tuple of values $\varphi_i=(w_i,b_i,\beta_i)$, comprising a weight value $w_i$ and an offset value $b_i$ and an activation function $\beta_i$.

In one or more embodiments, for instance, for respective first 162 and second 164 layer:
- a set of weighting values is referenced as W, W'
- a set of bias values is referenced as b, b',
- a set of activation functions is referenced as β,β'.

It is noted that even if the symbols used are different, the values and functions may be the same for the first 162 and second layers 164, e.g. first and second layer may have an equal set of activation function β'=β.

In one or more embodiments, the sets of activation function comprise sigmoid functions, for instance as $$\beta(x) \to \text{Sigmoid} \to (1+e^{-x})^{-1}$$

where x is the set of input values.

In one or more embodiments, the first and second processing stages 162, 164 may implement Stacked AutoEncoder (briefly, SAE) processing 161, with the purpose of learning to recognize patterns and providing features in the set of signals x, e.g. in an unsupervised manner.

In one or more embodiments, the first processing stage 162 may implement a first AutoEncoder ANN (briefly, encoder) while the second processing stage 164 may implement a second encoder.

In one or more embodiments, the first processing stage 162 may provide as a result y a so-called "latent representation" of the processed input signals indicative of, e.g. internal mapping of, the morpho-volumetric dynamic of the sampled PPG signal S.

In one or more embodiments, the second processing stage 162 may provide as a result y' a further latent representation, e.g. a further internal mapping, of the processed latent representation y of the processed input signals.

The encoder stages 162, 164 in the SAE stage 161 learn to compress data x from the input layer 160 into a code y, and then reconstruct from that code y a set of reconstructed signals z aiming to match the original dataset x, learning autonomously and providing a set of image features, e.g. encoded in the weight values W, W', in the process.

In one or more embodiments, the first encoder 162 and the second encoder 164 in the SAE stage 161 can be expressed via respective functions φ and φ', identifying tuples of values of perceptrons in respective layers, e.g.:

$$\varphi=\{W,b,\beta\}; \varphi'=\{W',b',\beta'\}$$

where the boldface indicates that the symbols are vectors (e.g. having size >1).

For instance, the latent representation y may be expressed as:

$$y=\theta(x)=\beta(Wx+b); W \in d'xd; b \in \mathbb{R}$$

while the set of reconstructed signals z may be expressed as:

$$z=\gamma(y)=\beta(W'y+b')$$

Accordingly, the stacked auto-encoder SAE 161 may be trained to minimize reconstruction errors, e.g. squared errors, by imposing constraints on the residuals, e.g. the residual difference between reconstructed z and original x sets of signals, for instance expressed as:

$$\varphi^*, \varphi'^* = \underset{\varphi, \varphi'}{\text{argmin}} \frac{1}{n}\sum_{i=1}^{n} L(x(i), z(i)) = \underset{\varphi, \varphi'}{\text{argmin}} \frac{1}{n}\sum_{i=1}^{n} L(x(i), \gamma(\beta(W'x+b')))$$

where the functional L(x(i), z(i)) is a variational functional which may be expressed as:

$$L(x(i), z(i)) = \sum_{j=1}^{n_h} \partial \log \frac{\partial}{\frac{1}{m}\sum_{i=1}^{m}\delta_j^{(a)}(x^{(i)})} + (1-\partial_j)\log \frac{1-\partial}{1-\left(\frac{1}{m}\sum_{i=1}^{m}\delta_j^{(a)}(x^{(i)})\right)}$$

In one or more embodiments, a KLD (Kullback-Leibler Divergence) method may be found suitable for use in training the SAE ANN processing stage 161, facilitating to avoid occurring in classical over-fitting problems for the network 161 (e.g. due to limited generalization) and improving the learning performances.

Accordingly, the objective function to minimize residuals may be modified, and may be expressed as:

$$\underset{\varphi, \varphi'}{\text{argmin}} \sum_{i=1}^{n} L(x(i), \gamma(\beta(Wx(i)+b))) + \tau \sum_{j=1}^{H_d} \mathcal{F}_{KL}(\rho\|\hat{\rho})$$

where $\mathcal{F}_{KL}(\rho\|\hat{\rho})$ stands for the Kullback-Leibler divergence operator, e.g. indicative of a measure of how one probability distribution p is different from a second, reference probability distribution $\hat{\rho}_j$, expressed as:

$$\mathcal{F}_{KL}(\rho\|\hat{\rho}) = \sum_{j=1}^{n_{th}} KL(\partial\|\partial_j)$$

wherein $$\partial_j \cong \frac{1}{m}\Sigma_{i=1}^{m}\delta_j^{(a)}(x^{(i)}),$$

hence implementing a Kullback-Leibler divergence.

In one or more embodiments, a further expression may be used, summarizing what discussed in the foregoing, for instance as:

$$J_{sparse}(W, b) = J(W, b) + \mu \sum_{j=1}^{n_{th}} KL(\tilde{\partial}||\partial_j) =$$

$$= J(W, b) + + + \mu$$

$$\left( \sum_{j=1}^{n_h} \tilde{\partial} \log \frac{\tilde{\partial}}{\frac{1}{m}\sum_{i=1}^{m} \delta_j^{(a)}(x^{(i)})} + (1 - \tilde{\partial}_j) \log \frac{1 - \tilde{\partial}}{1 - \left(\frac{1}{m}\sum_{i=1}^{m} \delta_j^{(a)}(x^{(i)})\right)} \right)$$

In one or more embodiments, the learned weights W in the first encoder stage 162 and the learned weights W' in the second encoder stage 162 may be included in the set of features SF3 provided by the ANN processing stage 48.

In one or more embodiments, the third set of features comprising for instance the reconstructed signal z, the first latent representation y, the second latent representation y', the first set of features W and/or the second set of features W' from the SAE stage 161.

Figure 11:
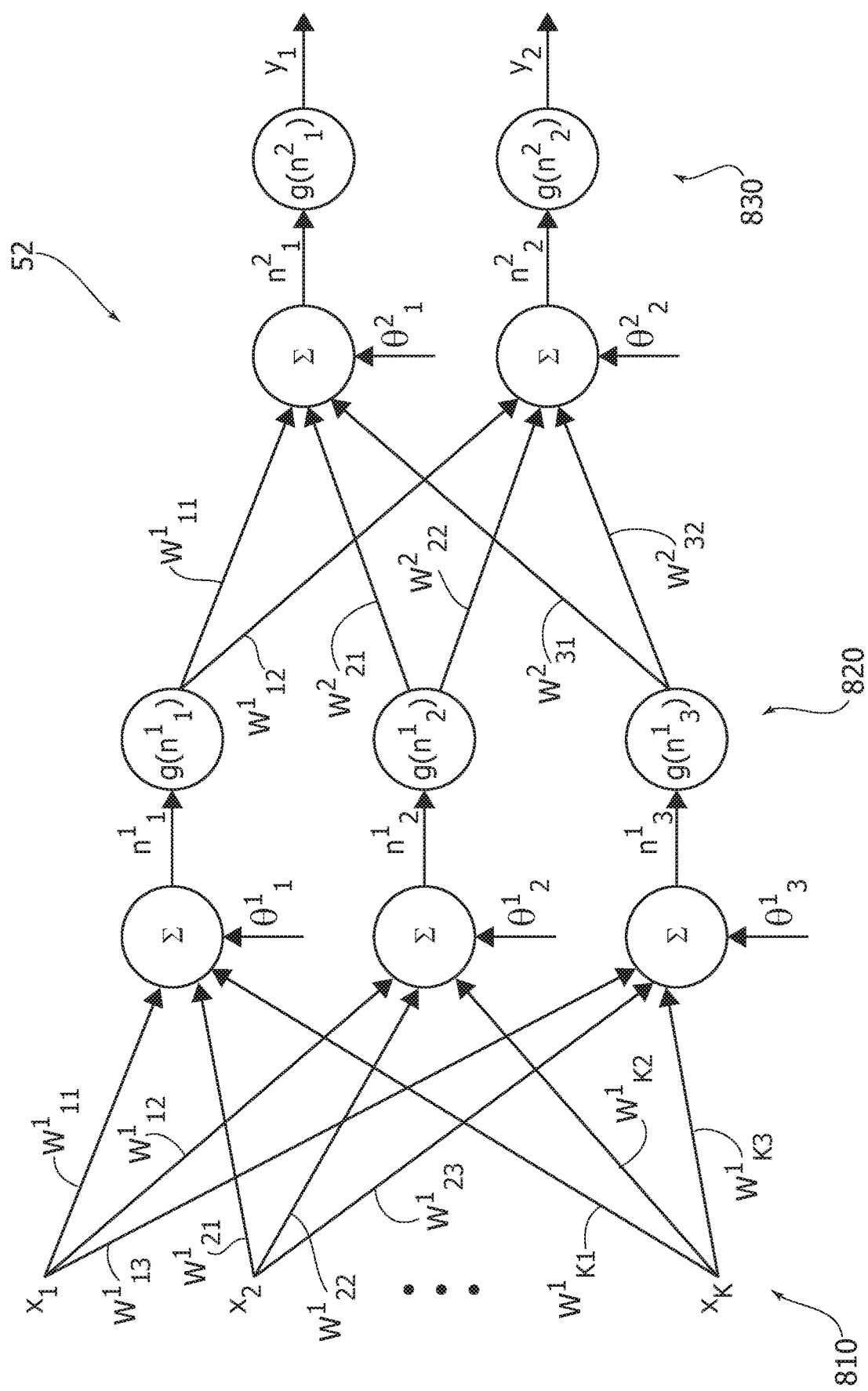

In one or more embodiments as exemplified in FIG. 11, a clustering layer, e.g. a softmax layer, is found suitable for use in the pattern recognition layer 50 in the pipeline 40 as per the present disclosure.

In one or more embodiments, the pattern recognition stage 50 may receive at least one of a first set of features SF1 provided by the hyper-filtering stage 44, a second set of features SF2 provided by the DTW processing stage 46, and/or a third set of features SF3 provided by the ANN processing stage 48, and may provide to the user circuit a grouping or clustering of the features indicative of a profile of a user.

In one or more embodiments, the set of features SF1; SF2, SF3 may be further processed in a pattern recognition processing stage 50 in the pipeline 100 which may employ an artificial network processing stage 52.

In one or more embodiments, a Scaled Gradient Conjugate Fully-Connected (briefly, SGC-FC) Regression method as exemplified in FIG. 8 may be found suitable for use in training the artificial neural network employed in the first pattern recognition processing stage 52.

For instance, such an artificial neural network 52 may be trained employing the method known from document M. Moller, "A Scaled Conjugate Gradient Algorithm for Fast Supervised Learning", Neural Networks, Vol. 6, pp. 525-533, '99, which discusses a supervised learning algorithm (Scaled Conjugate Gradient, SCG) with super-linear convergence rate.

The method may be based upon a class of optimization techniques well known in numerical analysis as the Conjugate Gradient Methods. SCG uses second order information from the neural network but requires only O(N) memory usage, where N is the number of weights in the network. SCG may yield a speed-up of at least an order of magnitude depending on the convergence criterion, e.g., the bigger demand for reduction in error the bigger the speed-up. SCG may be fully automated including no user dependent parameters and facilitate avoiding time-consuming line-searches.

In one or more embodiments, a Scaled Conjugate Gradient (SCG) method denotes the quadratic approximation to the error E in a neighborhood of a point.

As exemplified in FIG. 11, such an SGC-FC Regression layer in the first pattern recognition stage 52 may comprise:
an input layer 810, comprising input nodes x1, x2, . . . , xK, for corresponding input values x1, x2, . . . , xK,
at least one hidden layer 820, comprising hidden layer summation nodes Σ, providing respective weighted sums of input values with respective weights and hidden output nodes g(n11), g(n21), g(n31), and
an output layer 830, comprising summation nodes Σ of values from previous layers with respective weights and output nodes y1, y2.

In one or more embodiments as exemplified in FIG. 2, the set of features SF1, SF2, SF3 may be further processed in a second pattern recognition (or classification) processing stage 54.

Figure 12:
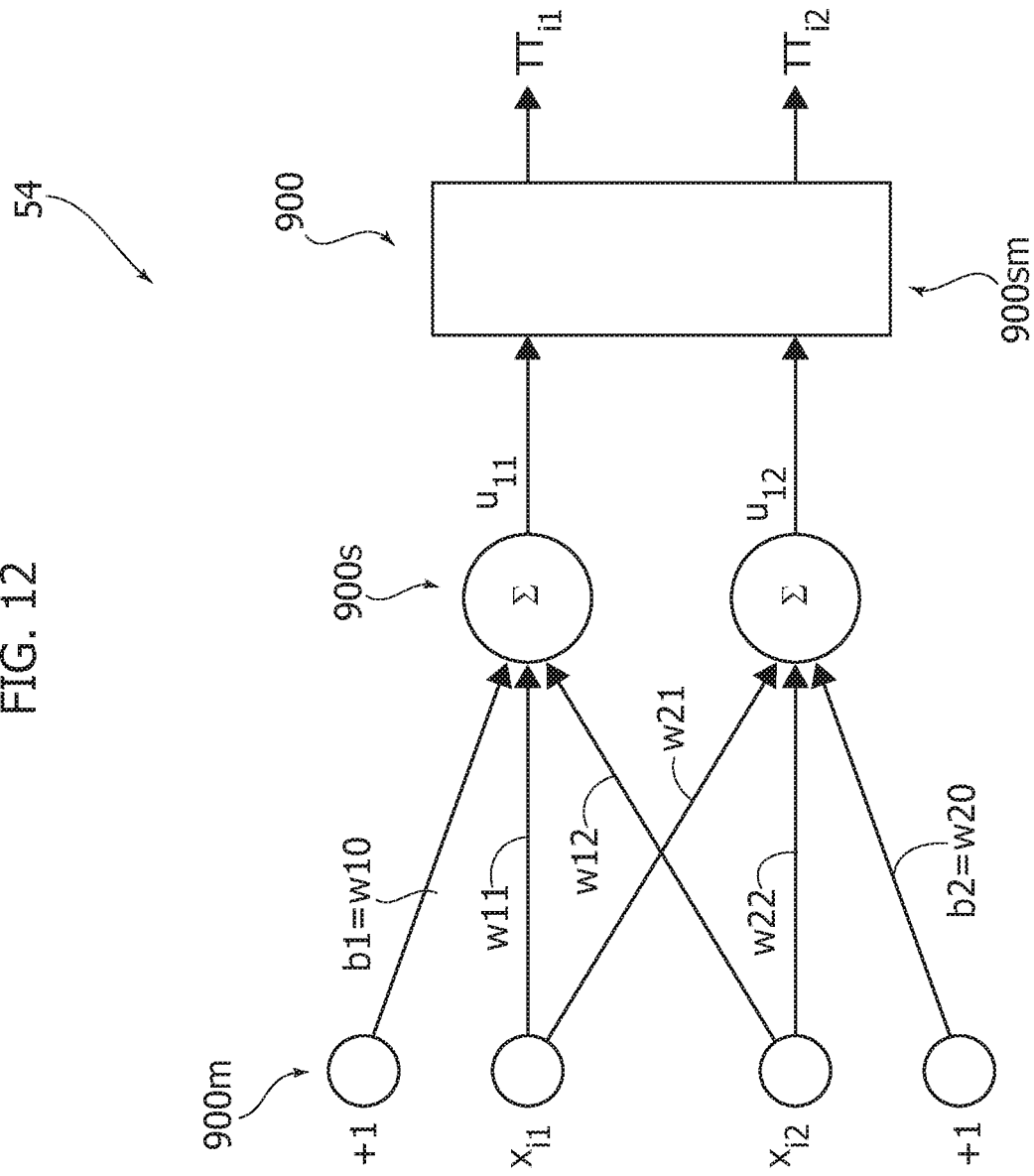

In one or more embodiments as exemplified in FIG. 12, a softmax layer 900 may be found suitable for use in the classification processing stage 54.

Softmax Regression layer is a generalization of logistic regression that may be found suitable for use for multi-class classification under the assumption that the classes are mutually exclusive: e.g., a profile of a user may be classified either as enabled/not enabled to ignite the vehicle or to activate other vehicle functions.

In one or more embodiments, the softmax layer 900 comprises a set of neurons 900 m, for instance m=4 neurons, configured to weight input data $x_{i1}$, $x_{i2}$ by respective weights $w_{11}$, $w_{12}$, $w_{12}$, $w_{22}$, $w_{20}$ and bias values +1. Weighted input data and bias values are then added therebetween in respective summation nodes 900s to provide a set of values $u_{11}$, $u_{12}$ onto which a softmax function is applied/computed. The softmax function may be represented as:

$$\Pi_{i1} = \frac{e^{x_i w_j}}{e^{x_i w_1} + e^{x_2 w_j}}$$

When applied to distinguish between two classes, as exemplified in FIG. 8, a softmax layer 900sm may compute respective softmax function values for each of the weighted input values for instance as:

$$\Pi_{i1} = \frac{e^{x_i w_j}}{e^{x_i w_1} + e^{x_2 w_j}} \text{ and}$$

$$\Pi_{i2} = \frac{e^{x_i w_j}}{e^{x_i w_2} + e^{x_2 w_2}} \text{ so that } \Pi_{i1} + \Pi_{i2} = 1$$

In one or more embodiments, the classification processing stage 60 may provide as output a signal P, e.g. having a value between 0 and 1, which may be used to recognize a "profile" of the driver and classify it as "enabled" or "not enabled" to use the vehicle. For instance, as a function of a threshold first value:
if the output signal P has a value between the first value, e.g. 0.0, and a second value, e.g. 0.5, the driver profile is classified as "not enabled" (class=0), if the output stage signal P has a value between a third value, e.g. 0.51, and a fourth value, e.g. 1.0, the driver profile is classified as "enabled" (class=1).

In one or more embodiments, the output signal P may be provided to user circuits A which may triggered to activate vehicle functions (e.g., ignition/start-up) when the classification is "enabled" while conversely sending an alert message when the classification is "not enabled". Hence, the signal P may be modeled as a virtual key which, when input into an appropriate receptor located onboard the vehicle V, may be suited or not to turn some or all vehicle functions.

One or more embodiments have been tested over electrophysiological signals, e.g. PPG signals, collected from thirty-two patients with different ages, sex, and so on. In one or more embodiments, the pattern recognition stage 50 artificial neural networks 52, 54 may be trained on a pre-disposed training set, e.g. stored in a memory circuit portion in the pipeline 100, comprising custom or pre-defined PPG signals collected, in order to learn to map adequately the set of signals to a set of classes, e.g. enabled to drive/not enabled to drive, etc.

In one or more embodiments, ANN training was performed using an INTEL i9 15 Cores together with a GPU TI GTX 2030 with CUDA ops in a time interval of approximately 100 seconds.

In one or more embodiments, processing the electrophysiological signal via artificial neural network processing and classification processing 50, 52, 54 as discussed herein may be implemented in a processing circuit of an Accordo 5 processor fabricated at STMicroelectronics.

One or more embodiments may comprise a method (for instance, 100), including:
collecting (for instance, 10, SB) at least one electrophysiological signal (for instance, S) of a human (for instance, F) over a limited time duration, wherein collecting (for instance, 10, SB) the at least one electrophysiological signal is discontinued at the expiry of the limited time duration,
computing (for instance, 44) a set of electrophysiological signal features (for instance, SF1, SF2, SF3) as a function of the electrophysiological signal collected, wherein the computing may comprise at least one of:
i) providing at least one reference electrophysiological signal (for instance, Sref) and applying dynamic time warping, DTW, processing (for instance, 46) to the at least one collected electrophysiological signal and to the at least one reference electrophysiological signal;
ii) applying stacked-auto-encoder artificial neural network, SAE ANN, processing (for instance, 48, 161) to the collected electrophysiological signal;
iii) filtering (for instance, 42) the electrophysiological signal collected via joint low-pass (for instance, 42a) and high-pass (for instance, 42b) filtering using a set of filtering parameters (for instance, FP) including low-pass filter parameters (for instance, 442a, 444a, 446a) and high-pass filter parameters (for instance, 442b, 444b, 446b) having a set of low-pass cut-off frequencies and a set of high-pass cut-off frequencies, respectively;
applying pattern recognition processing (for instance, 50) to the computed set of features, wherein the pattern recognition processing produces a virtual key signal (for instance, P) indicative of an identity of the human,
applying the virtual key signal to a user circuit (for instance, A) to switch the user circuit between a first state and a second state as a result of the virtual key signal matching an authorized key signal stored in the user circuit.

In one or more embodiments of the method, applying dynamic time warping, DTW, processing (for instance, 46) to the at least one collected electrophysiological signal and to the at least one reference electrophysiological signal may comprise:
providing a grid (for instance, 4620) comprising a plurality of empty grid cells, the grid configured to host the at least one collected electrophysiological signal as a first entry and the at least one reference electrophysiological signal as a first item, wherein the empty grid has a (maximum) number of entries which is a function of the reference electrophysiological signal and a (maximum) number of items which is a function of the collected electrophysiological signal,
generating (for instance, 464) at least one random value (for instance, K),
applying a ranking metrics based on at least one distance value (for instance, $d_{ij}$; $d_{ij}^1$) computed between the at least one collected electrophysiological signal and the at least one reference electrophysiological signal, wherein the distance value is computed as a function of the generated at least one random value and of the at least one collected electrophysiological signal and the at least one reference.

In one or more embodiments of the method, the SAE ANN processing (for instance, 48, 161) may comprise:
a first encoder layer (for instance, 162), configured to receive the collected electrophysiological signal and provide a first set of latent representations (for instance, y) and a first subset of features (for instance, W), and
a second encoder layer (for instance, 164), configured to receive the first set of latent representations and provide a second set of latent representations (for instance, y') and a second subset of features (for instance, W') of the collected electrophysiological signal.

In one or more embodiments of the method, applying pattern recognition processing (for instance, 50) to the computed set of features and producing the virtual key signal may comprise at least one of:
applying (for instance, 52) Scaled Conjugate Gradient Fully Connected layer (for instance, 810) neural network processing,
clustering (for instance, 54) the set of features by applying a set of softmax activation functions (for instance, g).

In one or more embodiments of the method, the at least one electrophysiological signal may be a PhotoPletysmoGraphy, PPG, signal collected from the driver (for instance, F) of a vehicle (for instance, V) via a PPG sensor (for instance, PD, 10) on board the vehicle (for instance, V).

In one or more embodiments of the method, the user circuit may be a driver assistance device (for instance, A) configured to operate a vehicle as a function of the virtual key signal.

One or more embodiments may comprise a vehicle-key device (for instance, SB) configured to be equipped onboard a vehicle (for instance, V), the vehicle-key device (for instance, SB) comprising:
a PhotoPletysmoGraphy, PPG, sensor (for instance, PD) configured to collect at least one electrophysiological signal (for instance, S), and
processing circuitry (for instance, 10) configured to process the at least one electrophysiological signal collected (for instance, S) with a method (for instance, 100) according to one or more embodiments.

One or more embodiments may comprise a vehicle (for instance, V) equipped with one or more embodiments of the vehicle-key device (for instance, SB) and with a vehicle ignition circuit (for instance, A), wherein the device is coupled to the vehicle ignition circuit.

In one or more embodiments, the vehicle (V) may be equipped with at least one driver assistance device (for instance, A) configured to be triggered as a function of the virtual key signal (for instance, P).

One or more embodiments may comprise a computer program product loadable in the memory of at least one processing circuit (for instance, 40) and comprising software code portions for executing the steps of one or more embodiments of a method (for instance, 100) when the product is run on at least one processing circuit.

It will be otherwise understood that the various individual implementing options exemplified throughout the figures accompanying this description are not necessarily intended to be adopted in the same combinations exemplified in the figures. One or more embodiments may thus adopt these (otherwise non-mandatory) options individually and/or in different combinations with respect to the combination exemplified in the accompanying figures.

Without prejudice to the underlying principles, the details and embodiments may vary, even significantly, with respect to what has been described by way of example only, without departing from the extent of protection. The extent of protection is defined by the annexed claims.

What is claimed is:

1. A method comprising:
    collecting at least one electrophysiological signal of a human over a limited time duration;
    discontinuing the collecting at an expiry of the limited time duration;
    computing a set of electrophysiological signal features as a function of the at least one collected electrophysiological signal, the computing comprising at least one of:
        i) providing at least one reference electrophysiological signal and applying dynamic time warping processing to the at least one collected electrophysiological signal and to the at least one reference electrophysiological signal;
        ii) applying stacked-auto-encoder artificial neural network (SAE ANN) processing to the at least one collected electrophysiological signal; or
        iii) filtering the at least one collected electrophysiological signal via joint low-pass and high-pass filtering using a set of filtering parameters including low-pass filter parameters and high-pass filter parameters having a set of low-pass cut-off frequencies and a set of high-pass cut-off frequencies, respectively;
    applying pattern recognition processing to the computed set of electrophysiological signal features, the pattern recognition processing producing a virtual key signal indicative of an identity of the human; and
    applying the virtual key signal to a user circuit to switch the user circuit between a first state and a second state as a result of the virtual key signal matching an authorized key signal stored in the user circuit.

2. The method of claim 1, wherein the applying the dynamic time warping processing to the at least one collected electrophysiological signal and to the at least one reference electrophysiological signal comprises:
    providing a grid comprising a plurality of empty grid cells, the grid configured to host the at least one collected electrophysiological signal as a first entry and the at least one reference electrophysiological signal as a first item, the grid having a number of entries which is a function of the at least one reference electrophysiological signal and a number of items which is a function of the at least one collected electrophysiological signal;
    generating at least one random value; and
    applying ranking metrics based on at least one distance value computed between the at least one collected electrophysiological signal and the at least one reference electrophysiological signal, the distance value being computed as a function of the generated at least one random value and of the at least one collected electrophysiological signal and the at least one reference electrophysiological signal.

3. The method of claim 1, wherein the SAE ANN processing comprises:
    a first encoder layer, configured to receive the at least one collected electrophysiological signal and provide a first set of latent representations and a first subset of features, and
    a second encoder layer, configured to receive the first set of latent representations and provide a second set of latent representations and a second subset of features of the at least one collected electrophysiological signal.

4. The method of claim 1, wherein the applying the pattern recognition processing to the computed set of electrophysiological signal features and producing the virtual key signal comprises at least one of:
    applying Scaled Conjugate Gradient Fully Connected layer neural network processing; or
    clustering the set of electrophysiological signal features by applying a set of softmax activation functions.

5. The method of claim 1, wherein the at least one collected electrophysiological signal is at least one PhotoPletysmoGraphy (PPG) signal, and the collecting comprises collecting the at least one PPG signal from a driver of a vehicle via a PPG sensor on board the vehicle.

6. The method of claim 1, wherein the user circuit is a driver assistance device configured to operate a vehicle as a function of the virtual key signal.

7. A vehicle-key device configured to be equipped onboard a vehicle, the vehicle-key device comprising:
    a PhotoPletysmoGraphy (PPG) sensor configured to collect at least one electrophysiological signal of a human; and
    processing circuitry configured to:
        receive the at least one collected electrophysiological signal over a limited time duration;
        discontinue the receiving at an expiry of the limited time duration;
        compute a set of electrophysiological signal features as a function of the at least one collected electrophysiological signal, wherein the computing comprises at least one of:
            i) provide at least one reference electrophysiological signal and apply dynamic time warping processing to the at least one collected electrophysiological signal and to the at least one reference electrophysiological signal;
            ii) apply stacked-auto-encoder artificial neural network (SAE ANN) processing to the at least one collected electrophysiological signal; or
            iii) filter the at least one collected electrophysiological signal via joint low-pass and high-pass filtering using a set of filtering parameters including low-pass filter parameters and high-pass filter parameters having a set of low-pass cut-off frequencies and a set of high-pass cut-off frequencies, respectively;

apply pattern recognition processing to the computed set of electrophysiological signal features, wherein the pattern recognition processing produces a virtual key signal indicative of an identity of the human; and apply the virtual key signal to a user circuit to switch the user circuit between a first state and a second state as a result of the virtual key signal matching an authorized key signal stored in the user circuit.

8. The vehicle-key device of claim 7, wherein the processing circuitry configured to apply the dynamic time warping processing to the at least one collected electrophysiological signal and to the at least one reference electrophysiological signal comprises the processing circuitry configured to:

provide a grid comprising a plurality of empty grid cells, the grid configured to host the at least one collected electrophysiological signal as a first entry and the at least one reference electrophysiological signal as a first item, wherein the grid has a number of entries which is a function of the at least one reference electrophysiological signal and a number of items which is a function of the at least one collected electrophysiological signal;

generate at least one random value; and apply ranking metrics based on at least one distance value computed between the at least one collected electrophysiological signal and the at least one reference electrophysiological signal, wherein the distance value is computed as a function of the generated at least one random value and of the at least one collected electrophysiological signal and the at least one reference electrophysiological signal.

9. The vehicle-key device of claim 7, wherein the SAE ANN processing comprises:

a first encoder layer, configured to receive the at least one collected electrophysiological signal and provide a first set of latent representations and a first subset of features, and a second encoder layer, configured to receive the first set of latent representations and provide a second set of latent representations and a second subset of features of the at least one collected electrophysiological signal.

10. The vehicle-key device of claim 7, wherein the processing circuitry configured to apply the pattern recognition processing to the computed set of electrophysiological signal features and produce the virtual key signal comprises the processing circuitry configured to:

apply Scaled Conjugate Gradient Fully Connected layer neural network processing; and cluster the set of electrophysiological signal features by applying a set of softmax activation functions.

11. The vehicle-key device of claim 7, wherein the PPG sensor is on board the vehicle.

12. The vehicle-key device of claim 7, wherein the user circuit is a driver assistance device configured to operate the vehicle as a function of the virtual key signal.

13. A vehicle comprising:

a vehicle ignition circuit; and a vehicle-key device coupled to the vehicle ignition circuit, the vehicle-key device comprising:

a PhotoPletysmoGraphy (PPG) sensor configured to collect at least one electrophysiological signal of a human; and processing circuitry configured to:

receive the at least one collected electrophysiological signal over a limited time duration;

discontinue the receiving at an expiry of the limited time duration;

compute a set of electrophysiological signal features as a function of the at least one collected electrophysiological signal, wherein the computing comprises at least one of:

i) provide at least one reference electrophysiological signal and apply dynamic time warping processing to the at least one collected electrophysiological signal and to the at least one reference electrophysiological signal;

ii) apply stacked-auto-encoder artificial neural network (SAE ANN) processing to the at least one collected electrophysiological signal; or iii) filter the at least one collected electrophysiological signal via joint low-pass and high-pass filtering using a set of filtering parameters including low-pass filter parameters and high-pass filter parameters having a set of low-pass cut-off frequencies and a set of high-pass cut-off frequencies, respectively;

apply pattern recognition processing to the computed set of electrophysiological signal features, wherein the pattern recognition processing produces a virtual key signal indicative of an identity of the human; and apply the virtual key signal to a user circuit to switch the user circuit between a first state and a second state as a result of the virtual key signal matching an authorized key signal stored in the user circuit.

14. The vehicle of claim 13, further comprising:

at least one driver assistance device configured to be triggered as a function of the virtual key signal.

15. A computer program product loadable stored in a non-transitory memory of at least one processing circuit and comprising software code portions that, when the product is run on the at least one processing circuit, execute the following steps:

collecting at least one electrophysiological signal of a human over a limited time duration;

discontinuing the collecting at an expiry of the limited time duration;

computing a set of electrophysiological signal features as a function of the at least one collected electrophysiological signal, the computing comprising at least one of:

i) providing at least one reference electrophysiological signal and applying dynamic time warping processing to the at least one collected electrophysiological signal and to the at least one reference electrophysiological signal;

ii) applying stacked-auto-encoder artificial neural network (SAE ANN) processing to the at least one collected electrophysiological signal; or iii) filtering the at least one collected electrophysiological signal via joint low-pass and high-pass filtering using a set of filtering parameters including low-pass filter parameters and high-pass filter parameters having a set of low-pass cut-off frequencies and a set of high-pass cut-off frequencies, respectively;

applying pattern recognition processing to the computed set of electrophysiological signal features, the pattern recognition processing producing a virtual key signal indicative of an identity of the human; and applying the virtual key signal to a user circuit to switch the user circuit between a first state and a second state as a result of the virtual key signal matching an authorized key signal stored in the user circuit.

16. The computer program product of claim 15, wherein the applying the dynamic time warping processing to the at least one collected electrophysiological signal and to the at least one reference electrophysiological signal comprises:

providing a grid comprising a plurality of empty grid cells, the grid configured to host the at least one collected electrophysiological signal as a first entry and the at least one reference electrophysiological signal as a first item, the grid having a number of entries which is a function of the at least one reference electrophysiological signal and a number of items which is a function of the at least one collected electrophysiological signal;

generating at least one random value; and applying ranking metrics based on at least one distance value computed between the at least one collected electrophysiological signal and the at least one reference electrophysiological signal, the distance value being computed as a function of the generated at least one random value and of the at least one collected electrophysiological signal and the at least one reference electrophysiological signal.

17. The computer program product of claim 15, wherein the SAE ANN processing comprises:

a first encoder layer, configured to receive the at least one collected electrophysiological signal and provide a first set of latent representations and a first subset of features, and a second encoder layer, configured to receive the first set of latent representations and provide a second set of latent representations and a second subset of features of the at least one collected electrophysiological signal.

18. The computer program product of claim 15, wherein the applying the pattern recognition processing to the computed set of electrophysiological signal features and producing the virtual key signal comprises at least one of:

applying Scaled Conjugate Gradient Fully Connected layer neural network processing; or clustering the set of electrophysiological signal features by applying a set of softmax activation functions.

19. The computer program product of claim 15, wherein the at least one collected electrophysiological signal is at least one PhotoPletysmoGraphy (PPG) signal, and the collecting comprises collecting the at least one PPG signal from a driver of a vehicle via a PPG sensor on board the vehicle.

20. The computer program product of claim 15, wherein the user circuit is a driver assistance device configured to operate a vehicle as a function of the virtual key signal.

* * * * *